(12) United States Patent
Tamaoki et al.

(10) Patent No.: US 8,980,872 B2
(45) Date of Patent: Mar. 17, 2015

(54) AGENT FOR PREVENTING AND/OR TREATING FUNCTIONAL GASTROINTESTINAL DISORDER

(75) Inventors: Satoru Tamaoki, Kawasaki (JP); Jun Sato, Kawasaki (JP); Katsuichi Sudo, Kawasaki (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 418 days.

(21) Appl. No.: 13/061,239

(22) PCT Filed: Sep. 24, 2009

(86) PCT No.: PCT/JP2009/066533
§ 371 (c)(1),
(2), (4) Date: Feb. 28, 2011

(87) PCT Pub. No.: WO2010/035751
PCT Pub. Date: Apr. 1, 2010

(65) Prior Publication Data
US 2011/0152517 A1 Jun. 23, 2011

(30) Foreign Application Priority Data
Sep. 26, 2008 (JP) .................. 2008-248932

(51) Int. Cl.
A61K 31/33 (2006.01)
C07D 498/00 (2006.01)
A61K 31/439 (2006.01)
A61K 9/16 (2006.01)
A61K 9/20 (2006.01)

(52) U.S. Cl.
CPC ............ *A61K 31/439* (2013.01); *A61K 9/1652* (2013.01); *A61K 9/2018* (2013.01); *A61K 9/2054* (2013.01)
USPC ........................................ 514/183; 540/456

(58) Field of Classification Search
None
See application file for complete search history.

(56) References Cited

U.S. PATENT DOCUMENTS 5,886,002 A 3/1999 Ferrari et al.

FOREIGN PATENT DOCUMENTS

| JP | 61-23192 | 6/1986 | |
|---|---|---|---|
| JP | 5-255085 | 10/1993 | |
| JP | 6-298768 | 10/1994 | |
| JP | 2755550 | 3/1998 | |
| JP | 10-226645 | 8/1998 | |
| JP | 2834951 | 10/1998 | |
| WO | 01/11077 | 2/2001 | |
| WO | 2006102536 | * 9/2006 | ............... C12N 1/21 |
| WO | 2007/103448 | 9/2007 | |
| WO | 2008/016708 | 2/2008 | |

OTHER PUBLICATIONS

"Pancreatic Cancer: Prevention", http://www.mayoclinic.com/health/pancreatic-cancer/DS00357/DSECTION=prevention, accessed Mar. 10, 2013).*
Saad. Alimentary Pharmacology and Therapeutics, 2006, 24, 475-92.*
Kemmer. European Journal of Gastroenterology and Hepatology, 1994, 6, 571-77.*
Supplementary European Search Report dated Jan. 30, 2012 in EP Application No. 09816166.4.
Anonymous: "Appendix A: A Rome III Diagnostic Criteria for FGIDs", Rome III The Functional Gastrointestinal Disorders, Third Edition, pp. 885-897, 2006.
A. I. Sharara et al., "A Randomized Double-Blind Placebo-Controlled Trial of Rifaximin in Patients with Abdominal Bloating and Flatulence", American Journal of Gastroenterology, vol. 101, No. 2, pp. 326-333, Feb. 1, 2006.
V. Mohan, "Rifaximin in a Patient with Relapsing Functional Gastrointestinal Symptoms", Gastroenterology & Hepatology, vol. 3, No. 1, Supplement 1, pp. 7-8, Jan. 2007.
English translation of the International Preliminary Report on Patentability and Written Opinion dated May 10, 2011.
Office Action issued Mar. 11, 2013 in corresponding Russian Application No. 2011116400, with English language translation thereof.
International Search Report issued Feb. 2, 2011 in International (PCT) Application No. PCT/JP2009/066533.
M. Pimentel et al., "The Effect of a Nonabsorbed Oral Antibiotic (Rifaximin) on the Symptoms of the Irritable Bowel Syndrome", Annals of Internal Medicine, vol. 145, No. 8, pp. 557-563, 2006.
A. L. Fumi et al., "Rifaximin Treatment for Symptoms of Irritable Bowel Syndrome", The Annals of Pharmacotherapy, vol. 42, pp. 408-412, Mar. 2008.
A. J. Lembo et al., "Antibiotics for the Treatment of Functional Gastrointestinal Symptoms: A Case Series", Practical Gastroenterology, pp. 33-36, Sep. 2007.
D. A. Drossman, "The Functional Gastrointestinal Disorders and the Rome III Process", Gastroenterology, vol. 130, No. 5, pp. 1377-1390, 2006.
H. L. DuPont et al., "A Randomized, Double-Blind, Placebo-Controlled Trial of Rifaximin to Prevent Travelers' Diarrhea", Annals of Internal Medicine, vol. 142, No. 10, pp. 805-812, May 17, 2005.

* cited by examiner

Primary Examiner — Noble Jarrell
(74) Attorney, Agent, or Firm — Wenderoth, Lind & Ponack, L.L.P.

(57) ABSTRACT

A method for preventing and/or treating a functional gastrointestinal disorder, comprising administering, to a subject with the functional gastrointestinal disorder, rifaximin as an effective ingredient. The functional gastroinstestinal disorder includes a functional esophageal disorder, a functional gastroduodenal disorder (e.g., a functional dyspepsia), a functional bowel disorder (e.g., a functional bloating, a functional diarrhea), a functional abdominal pain syndrome, a functional gallbladder and Sphincter of Oddi disorder, a functional anorectal disorder (e.g., a functional fecal incontinence, a functional anorectal pain, a functional defecation disorder), a functional disorder in neonates and toddlers (e.g., an infant functional diarrhea), a functional disorder in children and adolescents (e.g., a childhood functional abdominal pain, a childhood nonretentive fecal incontinence), and other diseases.

2 Claims, 1 Drawing Sheet

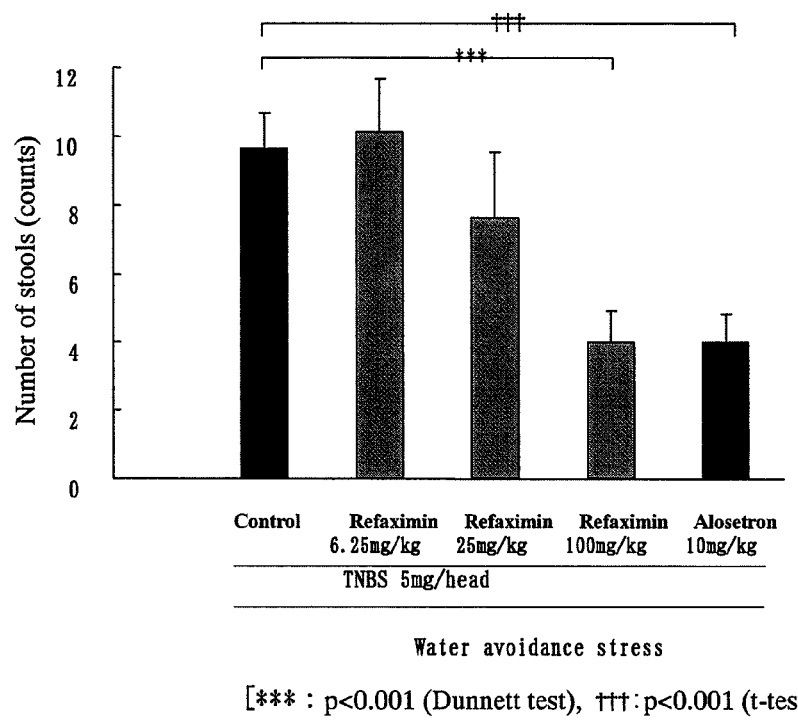

AGENT FOR PREVENTING AND/OR TREATING FUNCTIONAL GASTROINTESTINAL DISORDER

This application is a U.S. national stage of International Application No. PCT/JP2009/066533 filed Sep. 24, 2009.

TECHNICAL FIELD

The present invention relates to an agent for preventing and/or treating a functional gastrointestinal disorder, containing rifaximin as an effective ingredient.

BACKGROUND ART

Symptoms such as a diarrhea, a constipation, and an abdominal pain are observed in diseases with various organic changes of the gastrointestinal tract (e.g., an infection of the gastrointestinal tract and a tumor). On the other hand, such symptoms are also observed in many diseases in which no organic abnormality is recognized by an endoscopic examination or an examination using a contrast medium. Regarding diseases expressing these symptoms, global diagnostic criteria have been determined, and Rome III criteria have been published in 2006 as the current diagnostic criteria, which categorize diseases particularly based on the domain where a symptom is expressed. Patients have been classified into various diseases in accordance with these diagnostic criteria and received necessary medical treatments.

Moreover, many alimentary symptoms which are not categorized by the above diagnostic criteria are also observed. In actual clinical trials, the quality of life (QOL) of patients has been also evaluated. For example, in a clinical trial of a functional dyspepsia, Gastrointestinal Symptom Rating Scale (GSRS) has been widely used for estimating the QOL. The evaluation item includes (1) acid reflex, (2) abdominal pain, (3) indigestion, (4) diarrhea, (5) constipation and others, and has been graded and evaluated.

Heretofore, it has been difficult to identify a cause of development (or sideration) or to select a diagnostic or treatment technique for a functional gastrointestinal disorder in which no organic or pathologic change has been recognized. As a result, there has been some confusion, distrust, and misunderstanding among physicians, patients, and the general public. In addition, as described in Gastroenterol 130, 1377-1390, 2006 (Non-Patent Document 1), the tendency has been to overemphasize stress as the cause of development. At present, there is insufficient treatment technique for diseases categorized based on the diagnosis by the Rome III criteria or the like, except part of diseases. As the result of the disclosure of the diagnostic criteria, it has been further expected to clarify the cause of development of each disease or to study the corresponding precise treatment technique in the future. Thus, a control substance of a neurotransmitter (serotonin) involving or engaging to the motility of the intestinal tract was developed for a specific functional gastrointestinal disorder. However, after placing on the market, the control substance canceled a sale due to side effects thereof. Thus therapeutic drugs having no side effect have been strongly required.

On the other hand, Japanese Patent No. 61-23192 (JP-61-23192B, Patent Document 1) mentions that a compound "rifaximin" synthesized as a rifamycin derivative is an antibiotic having an activity to various species of a Gram-positive strain, a Gram-negative strain, an aerobic bacteria, and an anaerobic bacteria. Moreover, since rifaximin is not absorbed systemically, a first significant characteristic of rifaximin is to express no side effect when administered to the human body. Further, due to no systemic absorption, a second significant characteristic is to have neither adverse influence, in blood, to kinetics of other drugs which are used in combination with rifaximin nor drug interactions.

Rifaximin has been already widely used as a therapeutic agent for intestinal infection, hepatic encephalopathy, and skin infection. In addition, regarding rifaximin, the followings are mentioned: rifaximin has been marketed in the United States as a drug adaptable for the treatment of traveler's diarrhea (12 years of age or older) caused by noninvasive *Escherichia coli* [Annals of Internal Medicine, 142(10), p. 805-812, 2005 (Non-Patent Document 2)]; rifaximin is useful for preventing or treating bacterial colpopathy [Japanese Patent No. 2834951 (JP-2834951B, Patent Document 2)]; rifaximin is useful for preventing or treating gastric indigestion caused by *Helicobacter pylori* [Japanese Patent No. 2755550 (JP-2755550B, Patent Document 3)]; rifaximin is useful for preventing or treating diarrhea caused by cryptosporidiosis [Japanese Patent Application Laid-Open No. 226645/1998 (JP-10-226645A, Patent Document 4)]; rifaximin is useful for preventing or treating irritable bowel syndrome (IBS) or the like (International Publication WO 01/11077 pamphlet (Patent Document 5) and Annals of Internal Medicine, 145(8), p. 557-563, 2006 (Non-Patent Document 3)).

However, findings of rifaximin on a functional gastrointestinal disorder (particularly, a functional gastroduodenal disorder) have not been obtained. Moreover, an agent for preventing or treating a functional gastrointestinal disorder (particularly, a functional gastroduodenal disorder) containing rifaximin as an effective ingredient has not been known.

RELATED ART DOCUMENTS

Patent Documents

Patent Document 1: JP-61-23192B (Claim 1 and Column 23)
Patent Document 2: JP-2834951B (Claim 1)
Patent Document 3: JP-2755550B (Claim 1)
Patent Document 4: JP-10-226645A (Claim 1)
Patent Document 5: International Publication WO 01/11077 pamphlet (Claim 1)

Non-Patent Documents

Non-Patent Document 1: Gastroenterol 130, 1377-1390, 2006
Non-Patent Document 2: Annals of Internal Medicine, 142 (10), p. 805-812, 2005
Non-Patent Document 3: Annals of Internal Medicine, 145 (8), p. 557-563, 2006

SUMMARY OF THE INVENTION

Problems to be Solved by the Invention

It is therefore an object of the present invention to provide an agent useful for preventing and/or treating a functional gastrointestinal disorder.

It is another object of the present invention to provide an agent for preventing and/or treating a functional esophageal disorder, a functional gastroduodenal disorder, a functional bowel disorder, a functional abdominal pain syndrome, a functional gallbladder and Sphincter of Oddi disorder, a functional anorectal disorder, a functional disorder in neonates and toddlers, and/or a functional disorder in children and adolescents.

It is still another object of the present invention to provide an agent for preventing and/or treating a functional dyspepsia, a functional bloating, a functional diarrhea, a functional fecal incontinence, a functional anorectal pain, a functional defecation disorder, an infant functional diarrhea, a childhood functional abdominal pain, and/or a childhood nonretentive fecal incontinence.

It is a further object of the present invention to provide a preparation (a preventive and/or therapeutic agent) useful for preventing and/or treating the above-mentioned disease by improving an abnormal bowel function such as an abdominal pain, a diarrhea, or a constipation.

Means to Solve the Problems

The inventors of the present invention made intensive studies to achieve the above objects and finally found that rifaximin has curative activities against a functional gastrointestinal disorder (particularly, a functional gastroduodenal disorder, which is different from irritable bowel syndrome (IBS) in categories), particularly, an abnormal bowel function such as an abdominal pain, a diarrhea, or a constipation. The present invention was accomplished based on the above findings and further investigations.

That is, the present invention relates to an agent for preventing and/or treating a functional gastrointestinal disorder, which contains rifaximin as an effective ingredient. The functional gastrointestinal disorder may be a disease selected from the group consisting of a functional esophageal disorder, a functional gastroduodenal disorder, a functional bowel disorder, a functional abdominal pain syndrome, a functional gallbladder and Sphincter of Oddi disorder, a functional anorectal disorder, a functional disorder in neonates and toddlers, and a functional disorder in children and adolescents. Further, the functional gastrointestinal disorder may be a disease selected from the group consisting of a functional dyspepsia, a functional bloating, a functional diarrhea, a functional fecal incontinence, a functional anorectal pain, a functional defecation disorder, an infant functional diarrhea, a childhood functional abdominal pain, and a childhood nonretentive fecal incontinence. Furthermore, the functional gastrointestinal disorder may be a functional dyspepsia with an abnormal bowel function. The abnormal bowel function may be an abdominal pain, a diarrhea, or a constipation. According to the present invention, the number of stools can be reduced (or controlled or suppressed). Moreover, the present invention can normalize nature of stool. Further, the present invention can improve the motility of the intestinal tract. These effects of rifaximin would be never predicted from conventionally known pharmacological actions of rifaximin.

Effects of the Invention

The preventive and/or therapeutic agent of the present invention containing rifaximin as an effective ingredient improves an abnormal bowel function such as an abdominal pain, a diarrhea, or a constipation and is useful for preventing and/or treating a functional gastrointestinal disorder. Moreover, the agent of the invention is useful for preventing and/or treating a functional esophageal disorder, a functional gastroduodenal disorder, a functional bowel disorder, a functional abdominal pain syndrome, a functional gallbladder and Sphincter of Oddi disorder, a functional anorectal disorder, and/or a functional disorder in neonates and toddlers, and further, provides a preventive or therapeutic effect on a functional dyspepsia, a functional bloating, a functional diarrhea, a functional fecal incontinence, a functional anorectal pain, a functional defecation disorder, an infant functional diarrhea, a childhood functional abdominal pain, and/or a childhood nonretentive fecal incontinence. Further, the preventive and/or therapeutic agent of the invention has curative activities against a functional bowel disorder (such as an abdominal pain, a diarrhea, or a constipation) derived from the above-mentioned diseases. Therefore, according to the present invention, the number of stools can be reduced (or controlled or suppressed) and the nature of stool can be normalized. Furthermore, the present invention can improve or enhance the motility of the intestinal tract.

Moreover, rifaximin, which is a general-purpose compound for pharmaceutical preparations and shows no systemic absorption, has less side effects and enough safety.

BRIEF DESCRIPTION OF DRAWINGS

FIG. 1 is a graph for illustrating results in Example 1.

DESCRIPTION OF EMBODIMENTS

The preventive and/or therapeutic agent of the present invention contains rifaximin as an effective ingredient. Rifaximin may be either amorphous or crystalline. The crystal form of rifaximin is not particularly limited to a specific one and may be various polymorphs (e.g., crystalline polymorphs α, β, and γ).

Rifaximin can be produced by a conventional manner. For example, the details of the production process of rifaximin may be referred to the Patent Document 1 (JP-61-23192B), Japanese Patent Application Laid-Open No. 2007-509904 (JP-2007-509904A), International Publication WO 06/94662, and others.

Rifaximin has curative activities against a functional bowel disorder such as an abdominal pain, a diarrhea, or a constipation. Moreover, these curative activities can be realized through an antibacterial action on various bacteria or through a PXR receptor (pregnane X receptor), which is one of intranuclear receptors for protecting the living body from food or extraneous substances. The PXR receptor exists in stomach and duodenum (and other intestinal tract cells or cells involved or engaged in inflammation or immunisation, and the like) and bears or assumes a system for protecting the living body from extraneous substances. The PXR receptor functions for the protection of the living body not only in an inflammatory disease but also after recuperation of inflammation or in other functional gastrointestinal disorders with no accompanied by any organic change. Further, rifaximin is not systemically absorbed (that is, nonabsorbable) and has been used as a pharmaceutical component before. Accordingly, the preventive and/or therapeutic agent of the present invention has less side effects and established safety, and can be safely used for mammals (particularly, e.g., human beings). Further, rifaximin has a characteristic that does not produce resistant bacteria even in repeated administration.

The preventive and/or therapeutic agent of the present invention is effective for a functional gastrointestinal disorder. The functional gastrointestinal disorder shows higher incidence in gastroenterology and is an important disease category. The functional gastrointestinal disorder is categorized into many diseases by the Rome III criteria. In the Rome III criteria, gastrointestinal tract disorders expressing no organic disease is classified into A to H: "A: Functional esophageal disorders", "B: Functional gastroduodenal disorders (e.g., a functional dyspepsia)", "C: Functional bowel disorders (e.g., an irritable bowel syndrome (IBS))", "D: Functional abdominal pain syndrome", "E: Functional gallbladder and Sphincter of Oddi disorders", "F: Functional anorectal disorders", "G: Functional disorders: neonates and toddlers", and "H: Functional disorders: children and adolescents".

In these classifications, the present invention is preferably applied to the followings: "A: Functional esophageal disorders (e.g., A1. Functional heartburn, A2. Functional chest pain of presumed esophageal origin, A3. Functional dysphagia, A4. Globus (globus hystericus; dysphagia))", "B: Functional gastroduodenal disorders (e.g., B1. Functional dyspepsia (FD) (e.g., B1a. Postprandial distress syndrome (PDS), B1b. Epigastric pain syndrome (EPS)), B2. Belching disorders (e.g., B2a. Aerophagia, B2b. Unspecified excessive belching), B3. Nausea and vomiting disorders (e.g., B3a. Chronic idiopathic nausea (CIN), B3b. Functional vomiting, B3c. Cyclicvomiting syndrome (CVS)), B4. Rumination syndrome in adults)", "C: Functional bowel disorders (e.g., C2. Functional bloating, C4. Functional diarrhea, C5. Unspecified functional bowel disorder)", "D: Functional abdominal pain syndrome (FAPS)", "E. Functional gallbladder and Sphincter of Oddi disorders (e.g., E1. Functional gallbladder disorder, E2. Functional biliary Sphincter of Oddi disorder, E3. Functional pancreatic Sphincter of Oddi disorder)", "F: Functional anorectal disorders (e.g., F1. Functional fecal incontinence, F2. Functional anorectal pain (e.g., F2a. Chronic proctalgia (e.g., F2a1. Levator ani syndrome, F2a2. Unspecified functional anorectal pain), F2b. Proctalgia fugax), F3. Functional defecation disorders (e.g., F3a. Dyssynergic defecation, F3b. Inadequate defecatory propulsion)", "G: Functional disorders: neonates and toddlers (e.g., G1. Infant regurgitation, G2. Infant rumination syndrome, G3. Cyclic vomiting syndrome, G4. Infant colic, G5. Functional diarrhea)", "H: Functional disorders: children and adolescents (e.g., H1. Vomiting and aerophagia (e.g., H1a. Adolescent rumination syndrome, H1b. Cyclic vomiting syndrome (CVS), H1c. Aerophagia), H2. Abdominal pain-related functional gastrointestinal disorders (FGID) (e.g., H2a. Functional dyspepsia (FD), H2c. Abdominal migraine, H2d. Childhood functional abdominal pain (e.g., H2d1. Childhood functional abdominal pain syndrome)), H3. Constipation and incontinence (e.g., H3b. Nonretentive fecal incontinence)".

Further, the present invention is preferably applied to the followings: "B: Functional gastroduodenal disorders (e.g., a functional dyspepsia)", "C: Functional bowel disorders (e.g., a functional bloating, a functional diarrhea)", "D: Functional abdominal pain syndrome", "F: Functional anorectal disorders (e.g., a functional fecal incontinence, a functional anorectal pain, a functional defecation disorder)", "G: Functional disorders: neonates and toddlers (e.g., an infant functional diarrhea)", "H: Functional disorders: children and adolescents (e.g., a childhood functional abdominal pain, a childhood nonretentive fecal incontinence)".

In particular, the present invention is useful for preventing and/or treating a functional gastroduodenal disorder. The functional gastroduodenal disorder is the concept of symptoms caused by an abnormal function of the gastrointestinal tract in which stress is one of causes. In the Rome III criteria, the functional gastroduodenal disorder includes a functional dyspepsia, a belching disorder, a nausea and vomiting disorder, and a rumination syndrome in adults.

A functional dyspepsia, one of the functional gastroduodenal disorders, refers to diseases (symptoms) caused by an abnormal function of the gastrointestinal tract, excluding gastroesophageal reflux disease (GERD) and irritable bowel syndrome (IBS). The symptom thereof includes an abdominal pain, a diarrhea, or a constipation in bowel or intestine, and a heartburn, a bothersome postprandial fullness, or a gastralgia in esophagus or stomach. In the functional dyspepsia, there are some reported symptoms, e.g., abnormal motility of the gastrointestinal tract, duodenum juice or fat infusion, hyperalgesia due to balloon distension of the intestinal tract, and nervous system abnormalities. These symptoms act on the motility of the intestinal tract (Transit time) and trigger abnormal defecation or abnormal form (or appearance) of stool such as a diarrhea or a constipation. Therefore, it is important to evaluate the effects on the functional dyspepsia based on not only the symptom which is the diagnostic criteria but also the QOL evaluation according to GSRS or the like. In actual, regarding diarrhea symptom of the functional dyspepsia, it has been reported that about 80% of patients with functional dyspepsia has abnormal bowel habit (such as defecation), and about 20% of the 80% patients has diarrhea symptom (Aliment Pharmacol Ther. 2006 Jul. 14; 24(2): 405). The preventive and/or therapeutic agent of the present invention also has beneficial effects on a functional dyspepsia having such a symptom as an abdominal pain in the bowel, a diarrhea, or a constipation.

Incidentally, although IBS (irritable bowel syndrome) is classified as "C: Functional bowel disorders" in the Rome III criteria, this disease is different from diseases to which the present invention is applicable. For example, according to the Rome III criteria, IBS is defined as pain associated with change in bowel habit. IBS is distinct from a functional diarrhea characterized by loose stools and no pain, or a functional bloating when there is no change in bowel habit. Moreover, the functional dyspepsia includes bothersome postprandial fullness, early satiation, epigastralgia, or epigastric burning and is differ from IBS in these points. The duodenum, which is the beginning position of the helical movement of the intestinal tract, plays a role in whole control and regulation of the movement of the intestinal tract and maintains the function of the gastrointestinal tract in cooperation with a lower gastrointestinal tract. The abnormal bowel or intestinal function engages with functional dyspepsia significantly. According to the present invention, the movement of the intestinal tract or bowel can be improved or enhanced.

In addition, the above-mentioned diarrhea includes a conventional symptom, for example, osmotic diarrhea, secretory diarrhea, microscopic colitis (collagenous or lymphocytic colitis), exudative diarrhea, diarrhea caused by decrease in absorption time, malabsorptive diarrhea, and paradoxical diarrhea. In the present invention, the number of stools can be reduced (or controlled or suppressed), and the nature of stool can be normalized.

The preventive and/or therapeutic agent of the present invention contains rifaximin. The agent may comprise rifaximin alone as a pharmaceutical or be used as a pharmaceutical composition (or preparation) containing rifaximin in combination with a carrier (e.g., a pharmaceutically or physiologically acceptable carrier).

With respect to the pharmaceutical composition, the carrier may be suitably selected depending on the form of the composition or preparation (that is, the dosage form), the route of administration, the application, and others. The dosage form is not particularly limited to a specific one and may be a solid preparation (for example, powdered preparations, powders, granulated preparations (e.g., granules and microfine granules or the like), spherical or spheroidal preparations, pills, tablets (including sublingual tablets, orally disintegrating tablets, troches, chewable tablet, and others), capsules (including hard capsules, soft capsules, and microcapsules), dry syrups, suppositories, film-like preparations, and sheet-like preparations), a semisolid preparation (for example, gels, jellys, gumdrop-like preparations, and cake-like or paste preparations), a liquid preparation (for example, solutions, suspensions, emulsions, syrup, elixir, and injectable solutions (or injections)), and others. Moreover, sprays or aerosols of the powdered preparations and/or the liquid preparation may be also included. Incidentally, the capsules may be a capsule filled with a liquid or a capsule filled with a solid preparation (such as granules). Moreover, the preparation may be a lyophilized preparation. Further, the preparation of the present invention may be a preparation releasing the active ingredient(s) at a controlled rate, that is, a sustained release preparation or a rapid-release preparation. Incidentally, in aerosols utilized for an inhalant agent and others, a method for generating an aerosol is not particularly limited to a specific one. For example, a medically effective ingredient and a propellant (e.g., an alternative for chlorofluorocarbon) may be filled in a single hermetic container and sprayed. Moreover, a medically effective ingredient and a compressed gas (such as carbon dioxide or nitrogen gas) may be filled in separate containers and sprayed in the form of a nebulizer or an atomizer. Further, the preparation may be an oral dosage form or a parenteral dosage form (for example, collunariums and inhalants). Furthermore, the preparation may be topical or local administration form (e.g., solutions such as injections (aqueous injections, non-aqueous injections) and suspensions). The preparation of the present invention is practically a solid preparation (particularly, an oral administration form).

The carrier may be suitably selected, depending on the administration route and the application of preparation, from components (e.g., an excipient, a binder, a disintegrant, a lubricant, and a coating agent) listed in Japanese Pharmacopoeia, (1) Handbook of Pharmaceutical Excipients (Maruzen Company, ltd., (1989)), (2) Japanese Pharmaceutical Excipients Dictionary 2000 (Yakuji Nippo Ltd., issued March, 2002), (3) Japanese Pharmaceutical Excipients Dictionary 2005 (Yakuji Nippo Ltd., issued May, 2005), (4) Pharmaceutics, revised fifth edition (Nankodo, Co., Ltd. (1997)), and (5) Japanese Pharmaceutical Excipients 2003 (Yakuji Nippo Ltd., issued August, 2003). For example, the carrier for a solid preparation is practically at least one member selected from the group consisting of an excipient, a binder, and a disintegrant. An additive such as a lipid may be used as the carrier.

The excipient may include a saccharide or a sugar alcohol such as lactose, white sugar or refined sugar, glucose, sucrose, mannitol, sorbitol, or xylitol; a starch such as a corn starch or a potato starch; a polysaccharide such as a crystalline cellulose (including a microcrystalline cellulose); silicon dioxide or a silicate such as a light silicic anhydride or a synthetic aluminum silicate; and others. The binder may include a water-soluble starch such as a pregelatinized starch or a partially pregelatinized starch; a polysaccharide such as agar, gum acacia (or gum arabic), dextrin, sodium alginate, a tragacanth gum, a xanthan gum, a hyaluronic acid, pectin, or a sodium chondroitin sulfate; a synthetic polymer such as a polyvinylpyrrolidone, a poly(vinyl alcohol), a carboxyvinyl polymer, a polyacrylic polymer, a polylactic acid, or a polyethylene glycol; a cellulose ether such as a methyl cellulose, an ethyl cellulose, a carboxymethyl cellulose, a carboxymethyl cellulose sodium, a hydroxyethyl cellulose, a hydroxypropyl cellulose, or a hydroxypropylmethyl cellulose; and others. The disintegrant may include calcium carbonate, a carboxymethyl cellulose or a salt thereof (e.g., a carmellose, a carmellose sodium, and a carmellose calcium), a polyvinylpyrrolidone (e.g., a polyvinylpyrrolidone and a crosslinked polyvinylpyrrolidone (crosslinked povidone)), a low-substituted hydroxypropyl cellulose, and others. These carriers may be used singly or in combination.

For example, there may be used, as the coating agent, a saccharide or a sugar, a cellulose derivative such as an ethyl cellulose or a hydroxyethyl cellulose, a poly(oxyethylene glycol), a cellulose acetate phthalate, a hydroxypropylmethyl cellulose phthalate, a methyl methacrylate-(meth)acrylic acid copolymer, and eudragit (a copolymer of methacrylic acid and acrylic acid). The coating agent may be an enteric component (e.g., a cellulose phthalate, a hydroxypropylmethyl cellulose phthalate, and a methyl methacrylate-(meth)acrylic acid copolymer) or a gastric soluble component comprising a polymer (e.g., eudragit) containing a basic component such as a dialkylaminoalkyl(meth)acrylate. Moreover, the preparation may be a capsule having such an enteric component or gastric soluble component as a capsule shell.

In the carrier of the liquid preparation, an oil-based carrier may include an oil derived from plants or animals (e.g., an oil derived from vegetables such as a jojoba oil, an olive oil, a palm oil, or a cotton seed oil; and an oil derived from animals such as squalene), a mineral oil (e.g., a liquid petrolatum and a silicone oil), and others. An aqueous carrier may include water (e.g., a purified water or a sterile water, a distilled water for injection), a physiological saline, a Ringer's solution, a glucose solution, a water-soluble organic solvent [for example, a lower aliphatic alcohol such as ethanol or isopropanol; a (poly)alkylene glycol (e.g., ethylene glycol and a poly(ethylene glycol)); and glycerin], dimethyl isosorbide, dimethylacetamide, and others. Moreover, the carrier of the semisolid preparation may be selected from the carrier of the solid preparation and/or that of the liquid preparation. Further, the carrier of the semisolid preparation may contain a lipid.

The lipid may include a wax (e.g., a bees wax, a carnauba wax, a cacao butter, a lanolin, a paraffin, and a petrolatum), a higher (or long chain) fatty acid ester [e.g., an alkyl ester of a saturated or unsaturated fatty acid, and an ester of a fatty acid with a polyvalent alcohol (such as a poly($C_{2-4}$alkylene glycol), glycerin, or a polyglycerin) (e.g., a glyceride)], a hardened (or hydrogenated) oil, a higher alcohol (e.g., a saturated aliphatic alcohol such as stearyl alcohol and an unsaturated aliphatic alcohol such as oleyl alcohol), a higher fatty acid (e.g., linoleic acid, linolenic acid, oleic acid, and stearic acid), a metallic soap (e.g., a metal salt of a fatty acid, such as a sodium salt of palm oil fatty acid or calcium stearate), and others.

In the preparation, known additives can be suitably used depending on an administration route, a dosage form, and others. Such an additive may include, for example, a lubricant (e.g., a talc, magnesium stearate, and a poly(ethylene glycol) 6000), a disintegrant aid, an antioxidation agent or an antioxidant, an emulsifier (e.g., a variety of surfactants such as a nonionic surfactant), a dispersing agent, a suspending agent, a dissolving agent, a dissolution aid, a thickener (e.g., a water-soluble polymer such as a carboxyvinyl polymer, a poly(vinyl alcohol), a carrageen, or a gelatin; and a cellulose ether such as a carboxymethyl cellulose), a pH adjusting agent or a buffer (e.g., a citric acid-sodium citrate buffer), a stabilizer, an antiseptic agent or a preservative (e.g., a paraben such as methyl paraben or butyl paraben), a fungicide or antibacterial agent (e.g., a benzoic acid compound such as sodium benzoate), an antistatic agent, a corrigent or a masking agent (e.g., sweetening agent), a coloring agent (e.g., a dye and a pigment such as colcothar), a deodorant or a perfume (e.g., an aromatic substance), an algefacient, an antifoaming agent, an isotonizing agent, and a soothing agent. These additives may be used singly or in combination.

For example, for the injectable solution, usually, the dissolving agent, the dissolution aid, the suspending agent, the buffer, the stabilizer, the preservative, and others may be used as the additive in practical cases. Incidentally, for a powdery injection, which are dissolved or suspended in a solvent before administration, may be added conventional additive (s) used for a powdery injection.

Moreover, in a topically or locally administering preparation such as an inhalant preparation or a transdermally absorbable preparation, as the additive, usually, the dissolution aid, the stabilizer, the buffer, the suspending agent, the emulsifier, the preservative, and others may be practically used.

The pharmaceutical composition of the present invention may be prepared by using a carrier component in addition to an effective ingredient, and if necessary, an additive and the like, with a conventional preparation manner (for example, a production process described in Japanese Pharmacopoeia $15^{th}$ edition or a process in accordance with the production process). The solid preparation may be, for example, produced by using a powdery carrier (e.g., a carrier selected from the group consisting of a binder, an excipient, and a disintegrant) together with an effective ingredient (e.g., rifaximin, if necessary other components). For example, the granules may be prepared by granulating the effective ingredient and the carrier component through extrusion granulation, spray granulation, or other means, and if necessary regulating the size of the resulting granule. The tablets may be produced by mixing the granulated matter and the additive if necessary, and compression-molding the resultant mixture. Moreover, if necessary, the tablets may be coated for masking the taste or imparting enteric property or sustained action thereto with per se known methods. The capsules may be prepared by filling granules in a capsule. Further, the cake-like or paste solid preparations may be prepared by mixing and kneading the effective ingredient and the powdery carrier together with a wetting component (e.g., the liquid carrier, the gel carrier, the solid or semisolid carrier, and the additive). Further, the powdery preparations may be produced by mixing the effective ingredient and the powdery carrier, and if necessary other components (e.g., other carriers and other additives).

The rifaximin content of the preparation and the amount to be administered (or dose) of the preventive and/or therapeutic agent of the present invention may be suitably selected in accordance with the subject to be administered, the age, body weight, sex, and condition (e.g., a performance status and a condition of a disease) of the subject, the duration (or period or schedule) of administration, the dosage form, the method (or route) of administration, and others. The rifaximin content of the preparation is, for example, about 0.01 to 90% by weight, preferably about 0.05 to 80% by weight, and more preferably about 0.1 to 70% by weight (e.g., about 0.5 to 50% by weight) in terms of a solid content relative to the total amount of the agent.

The preventive and/or therapeutic agent of the present invention can be used for non-humans or mammals and usually is safely applied for human beings. The dose of rifaximin is, for example, usually about 1 to 3000 mg, preferably about 10 to 2000 mg (e.g., about 50 to 1700 mg), and more preferably about 100 to 1500 mg (e.g., about 500 to 1200 mg) to human beings per day when the agent is orally administered to a standard adult (weight of 65 kg). The preventive and/or therapeutic agent of the present invention may be administered once a day, or twice or more times (e.g., about twice to fifth times) per day. Incidentally, in consideration of the condition (e.g., a performance status and a condition of a disease), age, sex, and body weight of the patient, the route of the administration and the optimal amount of the agent are determined.

The preventive and/or therapeutic agent of the present invention may be used in combination with one or more other drugs as long as the combination does not have an adversely affect.

The drug which can be administered in combination with the agent (or co-administrable drug) may be a low-molecular weight drug, a polypeptide, an antibody, a vaccine, or others. For example, the drug may include a stomachic, a digestant, a digestive enzyme, an antacid, an antiemetic, an anti-constipation agent or a cathartic, a diarrhea therapeutic drug [e.g., an antimicrobial drug, a stegnotic, an adsorbent, a drug to depress intestinal tract motor, and an intestinal remedy], and a therapeutic drug for digestive ulcer. The therapeutic drug for digestive ulcer may include, for example, protective agents against factors causing damages in gastrointestinal tracts [e.g., an anti-stress agent such as antianxiety agent, a counteractive such as an antacid, and a gastric secretory inhibitor such as an anticholinergic drug, an antigastric drug, a muscarine receptor inhibitor, an H2 receptor inhibitor, or a proton pump inhibitor], a protective agent [e.g., a protective agent for ulcer focal site, an incarnant agent, an apophlegmatic, a mucosal microcirculation improver, and a prostaglandin preparation]. Further, if necessary, a crude drug (or a galenical), a vitamin compound (e.g., vitamin A, vitamin B, vitamin C, vitamin D, and vitamin E), a mineral compound, an amino acid compound, and others may be used.

When the preventive and/or therapeutic agent of the present invention is used in combination with other drugs, the dosage form is not particularly limited to a specific one. For example, the both may be prepared simultaneously and administered as a single preparation or may be prepared separately and administered simultaneously or separately through the same administration route. Moreover, the both may be prepared separately and administered simultaneously or separately through the different administration route.

The proportion of the other drugs may be, for example, about 0.01 to 500 parts by weight, preferably about 0.1 to 100 parts by weight, and more preferably about 0.5 to 50 parts by weight relative to 100 parts by weight of rifaximin.

INDUSTRIAL APPLICABILITY

Since the preventive and/or therapeutic agent of the present invention contains rifaximin as an effective ingredient, the agent has an excellent preventing and/or treating effect on a functional dyspepsia, and particularly on a functional gastroduodenal disorder. The agent has less side effects and a high safety. Accordingly, the preventive and/or therapeutic agent is effective for a pharmaceutical preparation or the like.

EXAMPLES

The following examples are intended to describe this invention in further detail and should by no means be interpreted as defining the scope of the invention.

Example 1

Inhibition Test of the Number of Stools Using Water Avoidance Stress-Induced Hyperdefecation Model Each of rats was freely allowed to have an enteral nutritional supplement, ELENTAL (0.25 g/mL; manufactured by Ajinomoto Co., Inc.) contained in a water-feeding bottle for seven days before a treatment with TNBS (2,4,6-trinitrobenzene sulfonic acid). The rats were fasted from the day before the TNBS administration day, and drinking water instead of ELENTAL was contained in the water-feeding bottle. On the day of the TNBS treatment (the rat: 8-week-old), 10 mL of physiological saline was intrarectally injected to the rat under anesthetization with ethyl ether to wash the enteral content. After the washing, the rat was allowed to stand longer than 2 hours, and 1 mL of 5 or 30 mg/head of TNBS in 40% ethanol/physiological saline (vehicle) was applied (injected) through the rectal injection under anesthetization with pentobarbital. Further, a silicone plug was inserted to the anus of the rat to stay the TNBS solution in the injection site, and the surrounding of the anus was fixed with an adhesive cloth elastic bandage (Elastopore). After about four hours of the TNBS treatment, the Elastopore and the silicone plug were removed from the rat, and 10 mL of physiological saline was intrarectally injected to the rat to discharge the enteral content. The animal was conventionally bled for four weeks from the TNBS treatment to recover from colitis. Moreover, to each of positive control rats, alosetron was orally administered singly before one hour of the stress loading.

To each of the rats which recovered from colitis, 0.5% by weight of Tween 80 as control (vehicle) or rifaximin (6.25 mg/kg, 25 mg/kg and 100 mg/kg) was orally administered for 9 days. Moreover, to each of positive control rats, alosetron (10 mg/kg) was orally administered singly before one hour of the water-stress loading. On the day of the measurement of the number of stools (the rat: 12-week-old), the animal was allowed to stand on a block (10 cm×5 cm×10 cm) installed in a water bath (about 50×30×40 cm, water depth: 5 cm) for one hour. However, each of animals on which no water environment stress was loaded (normal group) was allowed to stand in a waterless bath. The total number of stools excreted for the one hour after the animal was allowed to stand in the water bath was measured as the number of stools. Moreover, the nature of stools were compared and examined. The measured results are shown in FIG. 1.

As apparent from FIG. 1, the administration of 100 mg/kg of rifaximin decreased the number of stools compared with the control and was significantly effective ($p<0.001$, Dunnett test). Incidentally, the alosetron-administered group showed a significantly effect compared with the control group ($p<0.001$, t-test). Further, the defecation inhibition effect of rifaximin depended on the dose. In addition, normalization in the nature of stool was observed in the rifaximin-administered group. Accordingly, in the rifaximin-administered group, the motility of the intestinal tract was improved. Further, in the rifaximin-administered group, compared with the alosetron-administered group, the body weight or others was not influenced by the administration of rifaximin. Therefore, the safety of rifaximin is high to a living body.

Preparation Example 1

Tablet

Using the following ingredients, a tablet was obtained in accordance with a usual manner described in Japanese Pharmacopoeia. Incidentally, the following was a proportion (% by weight) in a tablet.

| | |
|---|---|
| Refaximin | 5% by weight |
| Lactose | 63% by weight |
| Corn starch | 30% by weight |
| Guar gum | 2% by weight |

Preparation Example 2

Tablet

Using the following ingredients, a tablet was obtained in accordance with a usual manner described in Japanese Pharmacopoeia. Incidentally, the following was a proportion (% by weight) in a tablet.

| | |
|---|---|
| Refaximin | 50% by weight |
| Crystalline cellulose | 30% by weight |
| Hydroxypropylmethyl cellulose | 5% by weight |
| Magnesium stearate | 5% by weight |
| Lactose | 10% by weight |

Preparation Example 3

Capsule

Using the following ingredients, a granule was obtained in accordance with a usual manner described in Japanese Pharmacopoeia. A capsule was obtained by filling the resulting granule in a gelatin capsule in an amount of about 250 mg per capsule. Incidentally, the following was a proportion (% by weight) relative to 100% by weight of the contents of the capsule.

| | |
|---|---|
| Refaximin | 40% by weight |
| Crystalline cellulose | 25% by weight |
| Carboxymethyl cellulose sodium | 5% by weight |
| Pectin | 3% by weight |
| Lactose | 27% by weight |

The invention claimed is:

1. A method for treating a functional gastrointestinal disorder, comprising administrating, to a subject with the functional gastrointestinal disorder, rifaximin as an effective ingredient, wherein the functional gastrointestinal disorder is a functional dyspepsia with a diarrhea caused by stress, and
   wherein the method (a) reduces a number of stools, (b) normalizes a nature of stool, or (c) reduces a number of stools and normalizes motility of intestinal tract.
2. The method according to claim 1, which normalizes motility of intestinal tract.

* * * * *